(12) United States Patent
Grünewald et al.

(10) Patent No.: US 8,168,960 B2
(45) Date of Patent: May 1, 2012

(54) METHOD FOR THE PRODUCTION OF A SAMPLE FOR ELECTRON MICROSCOPY

(75) Inventors: Wolfgang Grünewald, Chemnitz (DE); Alex Vogt, Buchs (CH); Alexander Gabathuler, Azmoos (CH)

(73) Assignee: LEICA MIKROSYSTEME GmbH, Vienna (AT)

( * ) Notice: Subject to any disclaimer, the term of this patent is extended or adjusted under 35 U.S.C. 154(b) by 295 days.

(21) Appl. No.: 12/529,849

(22) PCT Filed: Mar. 3, 2008

(86) PCT No.: PCT/CH2008/000085
§ 371 (c)(1),
(2), (4) Date: Sep. 3, 2009

(87) PCT Pub. No.: WO2008/106815
PCT Pub. Date: Sep. 12, 2008

(65) Prior Publication Data
US 2010/0025577 A1 Feb. 4, 2010

(30) Foreign Application Priority Data
Mar. 6, 2007 (CH) ......................................... 358/07

(51) Int. Cl.
*G21K 5/10* (2006.01)
(52) U.S. Cl. ............. 250/492.21; 250/492.1; 250/492.2; 250/492.22; 250/492.3; 250/306
(58) Field of Classification Search ................. 250/306, 250/307, 310, 311, 492.1, 492.2, 492.21, 250/492.22, 492.3
See application file for complete search history.

(56) References Cited

U.S. PATENT DOCUMENTS

| 5,009,743 | A | | 4/1991 | Swann | |
|---|---|---|---|---|---|
| 5,472,566 | A | * | 12/1995 | Swann et al. | 204/192.34 |
| 5,825,035 | A | * | 10/1998 | Mizumura et al. | 250/423 R |
| 5,986,264 | A | * | 11/1999 | Grunewald | 250/310 |
| 6,784,427 | B1 | * | 8/2004 | Grunewald et al. | 250/311 |
| 6,914,244 | B2 | * | 7/2005 | Alani | 250/307 |
| 7,002,152 | B2 | | 2/2006 | Grunewald | |
| 2004/0164242 | A1 | * | 8/2004 | Grunewald | 250/307 |
| 2004/0222082 | A1 | * | 11/2004 | Gopalraja et al. | 204/192.3 |
| 2006/0197017 | A1 | * | 9/2006 | Motoi et al. | 250/310 |
| 2007/0045560 | A1 | * | 3/2007 | Takahashi et al. | 250/442.11 |

FOREIGN PATENT DOCUMENTS

| EP | 1 447 656 A1 | 8/2004 |
|---|---|---|
| EP | 1 505 383 A1 | 2/2005 |

* cited by examiner

*Primary Examiner* — Michael Maskell
(74) *Attorney, Agent, or Firm* — Foley & Lardner LLP

(57) ABSTRACT

A probe (1) for electron microscopy is cut from a solid material. A sample surface (3) is configured on the same, which is treated with an ion beam (J) at a predetermined angle of incidence such that the material is ablated from the sample surface (3) by means of etching until the desired observation surface (20) is exposed on the sample (1) in the region of the incidence zone (4) of the ion beam (J), which enables the viewing (12) of the desired region of the sample (1) using an electron microscope. For this purpose, at least two stationary ion beams ($J_1$, $J_2$) are guided onto the sample surface (3) at a predetermined angle ($\alpha$) in alignment with each other such that the ion beams ($J_1$, $J_2$) at least come in contact with each other on the sample surface (3), or cross each other, and form an incidence zone (4) in that location, and that both the sample (1) and the ion beams ($J_1$, $J_2$) are not moved, and thus are operated in a stationary manner.

32 Claims, 6 Drawing Sheets

METHOD FOR THE PRODUCTION OF A SAMPLE FOR ELECTRON MICROSCOPY

The invention relates to a method for producing a specimen for electron microscopy, in which the specimen is cut out of a solid-state material.

BACKGROUND

Specimens for the electron microscopy can be prepared in various ways. In order to be able to view specimens with an electron microscope, these must be processed in an appropriately defined way by uncovering the observation surface to be viewed by means of an etching method. When viewing with a scanning electron microscope (SEM), the desired surface is viewed. When viewing the specimen with a transmission electron microscope (TEM), the specimen is thinned by the etching such that electron beams can be transmitted through the specimen in the TEM, and the specimen can be viewed in transmission. Here, the quality of the image resolution essentially depends on the quality of the specimen. Therefore, the specimen should be uniformly set to an appropriately desired surface area for the SEM method or to a desired defined thickness for the TEM method by an appropriately suitable etching operation. Here, it is important that during this etching operation, the specimen structure is not varied by the operation itself. For producing such a specimen, at first a piece of the material to be examined is mechanically sawed out of the specimen body and thereafter treated by etching in order to be able to subsequently examine the specimen with an SEM or TEM. The wet chemical etching method does not lead to the desired result in this regard. For this reason, nowadays the specimens are processed under vacuum with an ion beam by ion etching, such as sputter etching, for the high-quality electron microscopic viewings with an SEM or TEM. As an ion beam, for example, an Argon ion beam having a diameter of about 1 mm is used.

Meanwhile, specimens for the electron microscopy can be prepared in different ways. Nowadays, in particular three methods are known for processing specimens by way of ion beam etching.

The ion beam slope etching technique is a method which has been used for a long time now for preparing cross-section specimens for the scanning electron microscopy (SEM). In this method, a part of the specimen surface is covered with a mask. The uncovered part of the surface is ion etched until some kind of a slope is created. At this slope, the cross-sectional structure of the specimen can be examined. The cutting depths reached lie in the range between a few 2.0 µm and a maximum of 50 µm. The preparation times vary between some minutes and several hours depending on the material and the etching depth. In order to obtain a uniformly removed cutting surface, the specimen has to oscillate during etching. This particularly applies to structured materials having highly different sputter rates, as found in the semiconductor industry. The presently known methods and techniques used for producing a slope cut only make use of one single ion source or one single ion beam.

The increasing requirements, in particular in the field of microelectronics, go in the direction of high cutting depths of up to one mm or more with, at the same time, a short preparation time and an excellent preparation quality which cannot be achieved with this known method.

A further known preparation method is the so-called wire shadow method. The wire shadow method is used for producing TEM specimens with extremely large electron transparent areas (several mm long) (Patent EP 1 505 383 A1). Here, a thin wire or a fiber is adhered onto the surface of the specimen to be etched, and the specimen is bombarded perpendicularly to the surface with a conventional ion source. By the wire shadowing, a wedge-shaped specimen is created which is electron transparent at the thinnest point. The thickness of the specimens is previously mechanically reduced to about 100 µm. In order to avoid etching selectivities in the specimen material, the specimen oscillates during the etching operation. With this method, too, the requirements go in the direction of high etching depths, with, at the same time, a short etching time and an excellent specimen quality.

These requirements cannot be met with the current etching technique both for the slope cutting method and for the wire shadow method.

A further known and commonly used preparation method is the TEM standard preparation. During the ion beam preparation of TEM standard specimens a mechanically pre-prepared specimen having a diameter of about 3 mm and a thickness of about 20 to 50 µm is etched either with two ion sources from one specimen side or one ion source on each specimen side, i.e. simultaneously on the front and the rear side. During the etching operation the specimen rotates or oscillates in order to avoid etching structures. Alternatively, the ion beam can be moved relative to the specimen or both. With this method, too, the requirements in the direction of a high etching depth with, at the same time, a short etching time and an excellent specimen quality cannot be met or only at high expense.

SUMMARY

The invention is based on the object to eliminate the disadvantages of the prior art. In particular, an etching method is to be implemented which allows high cutting depths with a short preparation time, and with which a high economic efficiency can be obtained given a high reliability and a good achievable specimen quality.

The object is solved according to the invention by proceeding in accordance with the method described herein.

According to the invention, electron microscopic specimens are etched with at least two stationarily arranged ion beams which are directed onto the specimen surface at an angle and hit each other thereat. Here, the specimens are likewise not moved so that no relative movement exists between the ion beams and the specimen, as a result whereof the entire assembly is operated in a stationarily arranged way.

According to the invention, the method for producing a specimen for the electron microscopy is comprised of the following steps. The specimen is first cut out of a solid state material, for example, mechanically. An additional chemical and/or mechanical treatment is possible. Thereafter, a specimen surface formed on the specimen is treated with an ion beam at a predetermined angle of incidence such that material is removed from the specimen surface by ion etching until the desired viewing surface is uncovered at the specimen in the area of the zone of incidence of the ion beam, which viewing surface subsequently allows the viewing with an electron microscope in the desired area of the specimen, at least two stationary ion beams being guided onto the specimen surface at a predetermined angle with respect to one another such that the ion beams at least contact or intersect each other at the specimen surface and form a zone of incidence thereat, and that both the specimen and the ion beams are not moved and thus operated stationarily.

The present etching method makes it possible to view the resting specimen during the etching operation in high resolution with viewing means and thus to control the operation, preferably with a light microscope or a scanning electron microscope. This viewing should take place at least temporarily over the course of the entire etching operation.

Advantageously, the specimen is oriented with respect to the viewing means prior to the ion etching and is not moved any more during the etching operation.

During the etching operation, the specimen can additionally be cooled so that in particular a still higher beam power can be allowed which as a result allows still higher etching speeds, even given very sensitive specimens.

Thus, it is possible to obtain high cutting depths with a short preparation time. A high surface quality is achieved, and etching selectivities are kept low or avoided. The conditions for this can be optimally chosen and set at the assembly, for example by the selection of the angle between the ion beams, the angle of incidence of the ion beams on the specimen surface, the same or a different energy of the beams, the beam diameter, the beam current density and position of the beams in the area of incidence of the specimen. The values can be predetermined, set or varied individually and/or in combination. The values can also be varied or followed up according to a predetermined program, for example with an automated control, depending on the progress of the etching operation. Advantageously, for a TEM specimen at least three stationary ion beams are used which do not have to lie in one plane. For specimens according to the slope etching method or the wire shadow method, favorable results are already achieved with two stationary ion beams. Three or more ion beams will yield still better results, and then it is advantageous when these three or more ion beams are guided to the specimen lying in one single plane.

For the preparation of, for example, solder balls, the slope etching is very suitable. Given such structures, the application of an oscillation movement, in accordance with the known methods, results in a highly undesired "tunnel effect" due to the different resulting bombardment angles during the oscillation. By proceeding according to the invention, this can now be well suppressed by the use of several stationary ion beams and, if necessary, additionally by the use of different energies for the individual ion beams.

The ion beams can be generated with an own ion source for each beam, or advantageously at least two ion beams can also be generated with one single ion source, in that these are generated from a common source arrangement, such as a plasma, by extraction.

In a preferred embodiment three ion sources, integrated in one housing, are each arranged at an angle of 60° with respect to one another. The ion beams form a point of intersection which can be directed to a selected point or, respectively, zone of incidence on the specimen surface. The beams form a circle sector between 60° and 120°. In this connection, the beams must strike the specimen surface from different directions so that an angle between 0° and 180°, preferably between 20° and 160° with respect to the specimen surface is formed depending on the application (etching depth or etching width) and that a point of intersection of the individual beams is formed on a selectable zone of incidence on the specimen. The circle sector can be formed by two or more beams. This can be realized by several ion beams, extracted from one or more ion sources. The angle of the circle sector influences the cutting speed and the surface quality, respectively.

In a further preferred embodiment for the slope etching method, three ion sources each offset by 60° and forming a circle sector (60° to 120°) are used. By setting the angle size different results can be achieved and, as a result thereof, set as desired. A smaller angle, for example between 60° and 120°, results in a higher cutting speed, but, on the other hand, in particular with specimens having a high etching selectivity, in stronger defined privileged directions.

The ion energy of the beams lies in the range between 200 eV and 12 keV, preferably in the range between 500 eV and 8 keV. The ion energy of the single sources can be varied in order to achieve specific etching profiles.

By the contacting and/or overlapping of the individual ion beams from different directions in an intersection area at the zone of incidence of the specimen surface, the above-mentioned sector of bombardment is formed which makes a rotation of the specimen for preventing privileged directions unnecessary. The position of the intersection area can be adjusted or even regulated, even during the etching operation. As a result thereof, the profile of the individual beam has less influence, and the method is less critical in its settings, as a result whereof the reliability is increased.

Ion energy and current density are, for example, also selectable depending on the thermal sensitivity of the specimen. Thus, by the specific adjustability of important parameters the presented method allows a high degree of flexibility in process control, which makes an adaptation to the most different specimens easily possible and this with high process productivity.

The invention will now be explained in more detail by way of an example with reference to schematic drawings.

DETAILED DESCRIPTION

Figure 2:
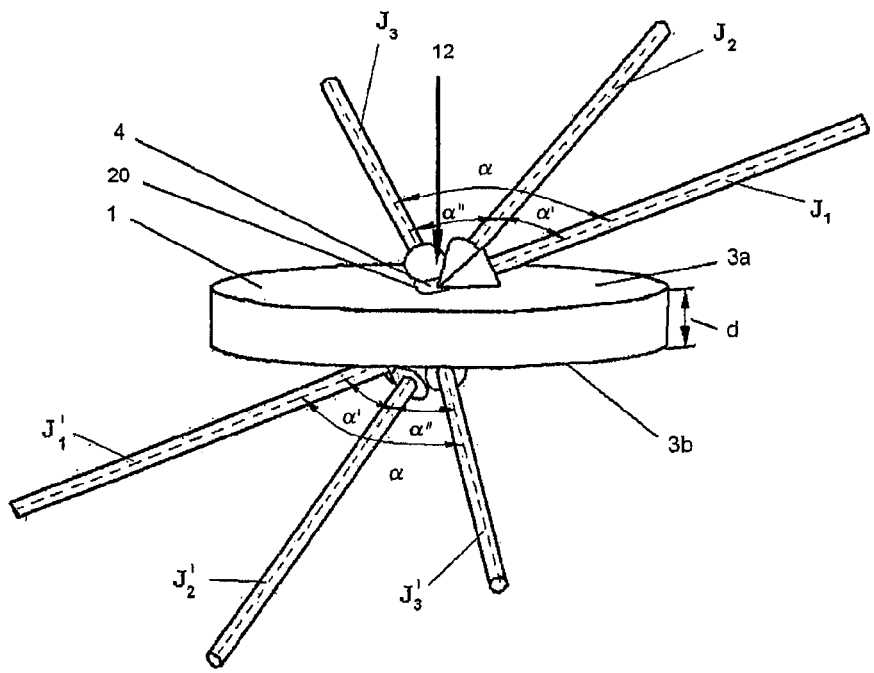
FIG. 2 shows a specimen in a three-dimensional illustration for a TEM standard specimen with etching on both sides with three ion beams each according to the invention.
Figure 5:
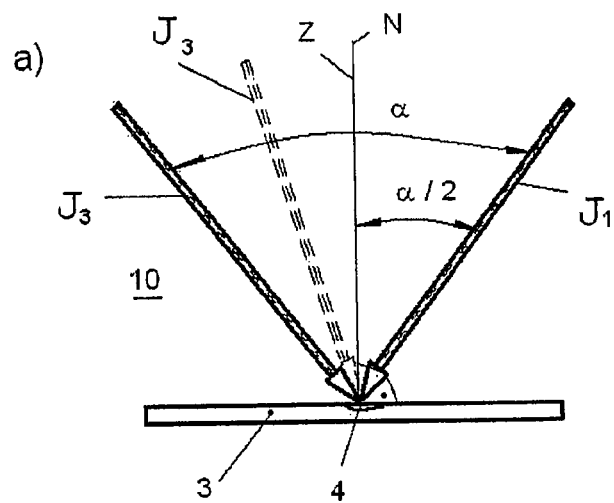
FIGS. 5a-c show cross-sections of ion beams lying in one plane at different possible angles with respect to one another and at different possible angles of incidence onto the specimen surface.
Figure 5:
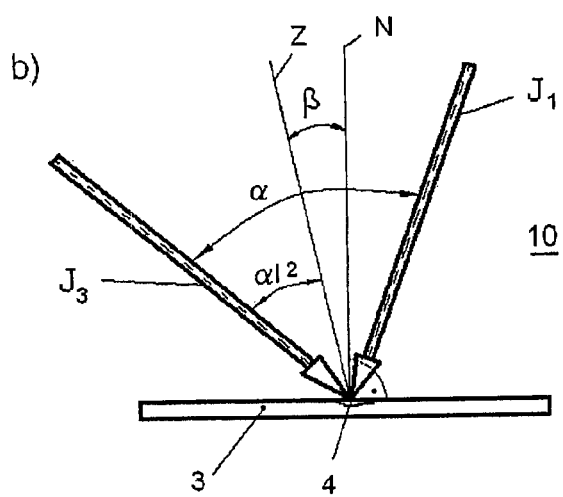
Figure 5:
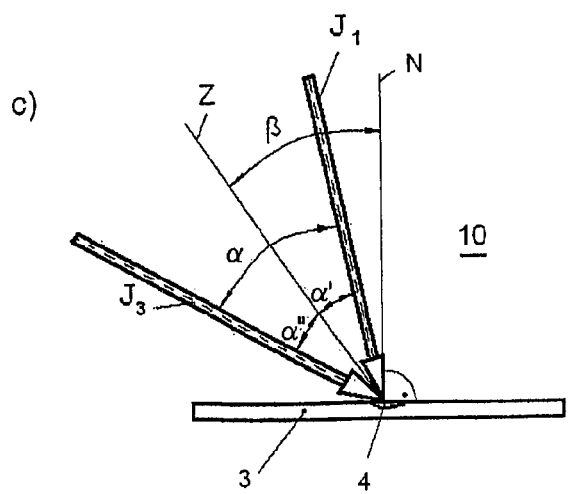
Figure 6:
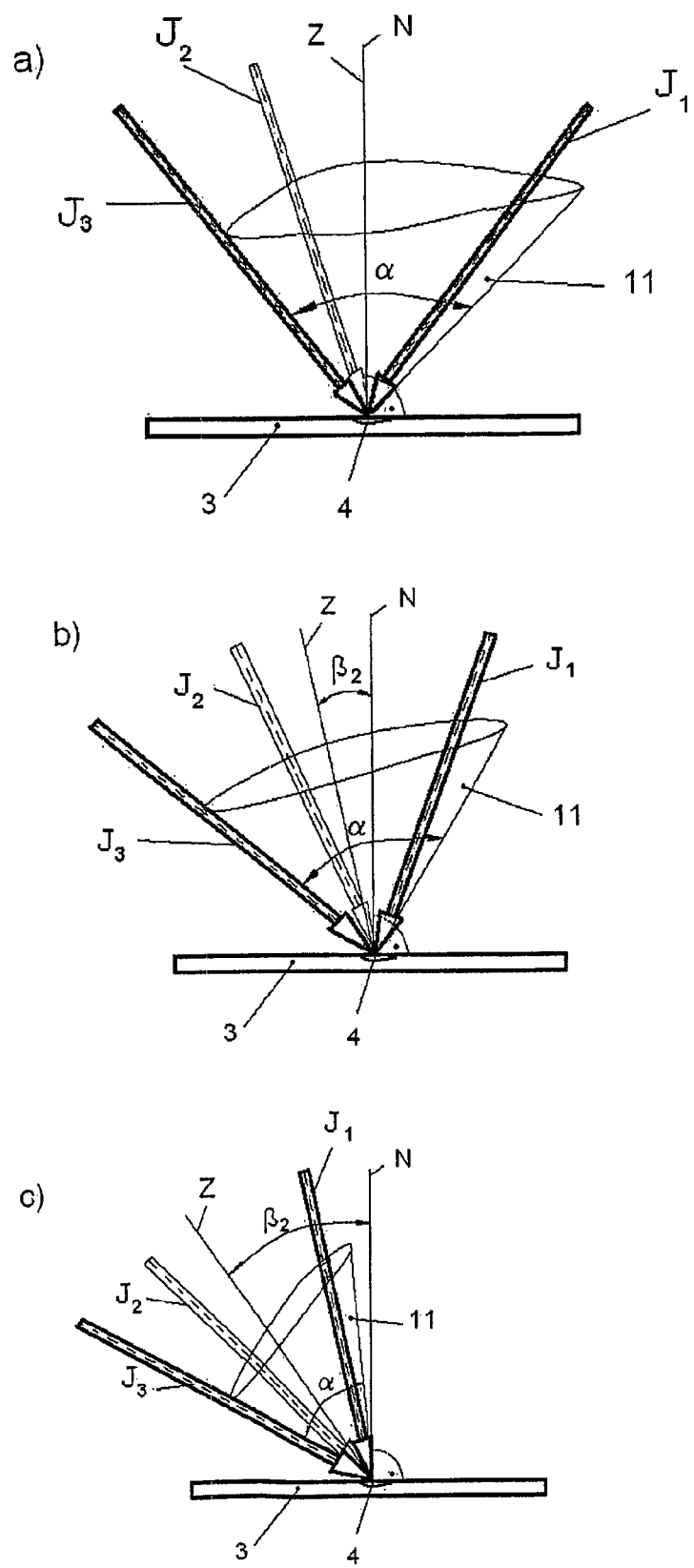
FIGS. 6a-c show cross-sections of ion beams lying on a conical surface at different possible angles with respect to one another and at different possible angles of incidence onto the specimen surface.
Figure 7:
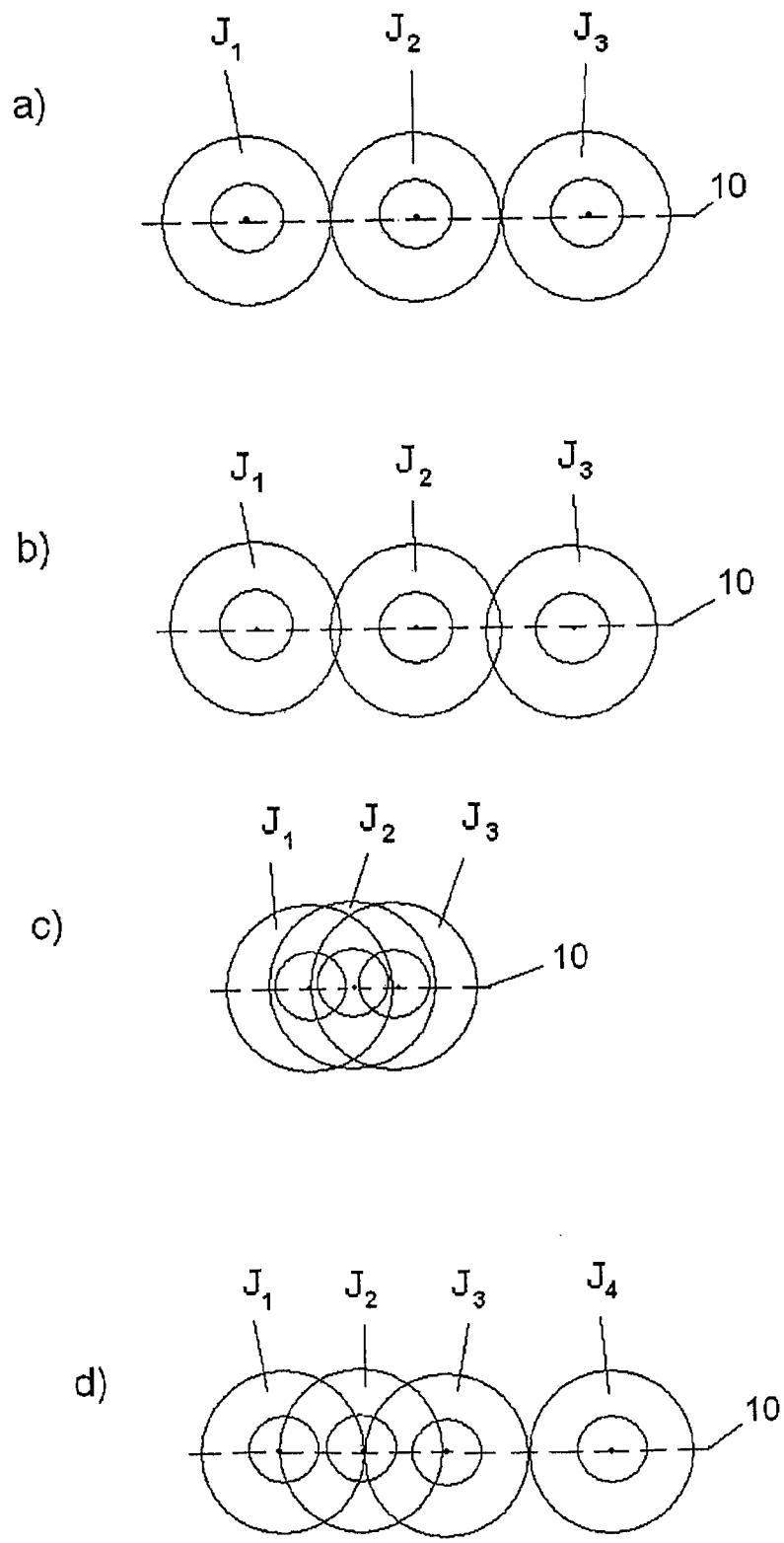
FIGS. 7a-d show, in top views of the specimen surface, different possible forms of the zone of incidence for several ion beams, given contacting and/or overlapping of ion beams lying in one line, for ion beams lying in one plane.

A flat specimen body 1 is, for example, cut out of the material to be examined with the aid of a diamond tool and is mechanically polished on both sides. The specimen 1 then has two sides, with the two surfaces 3a and 3b and the thickness d, as illustrated in FIG. 2. This is a typical specimen, as is usual for TEM viewings with the viewing direction 12 of the electron microscope and, is treated with only one ion beam according to the TEM standard etching method, where the specimen 1 or the ion beam is moved. According to the invention, the specimen surface 3 is now etched on one side or on both sides 3a, 3b simultaneously with at least two ion beams $J_1$, $J_2$, $J'_1$, $J'_2$ which contact or overlap each other in the zone of incidence 4 of the specimen surface 3. The assembly is stationarily operated, thus neither the specimen 1 nor the ion beams J are moved relative to one another. Even better results are achieved when at least three ion beams $J_1$, $J_2$, $J_3$ are used, and these all contact and/or overlap each other in the zone of incidence 4. The two ion beams J are guided onto the specimen surface 3 at an angle α. Thus, these form some kind of a circle sector and span a plane 10. If, for example, three ion beams $J_1$ to $J_3$ are used at the angles α, α', α" with respect to one another, these can be arranged in one single plane 10 (FIG. 5a) or on a conical circumferential surface 11, or if more than three ion beams are used, individual ion beams J can also be positioned with the cone (FIG. 6). The top of the cone, where all the ion beams J converge, is each time located in the area of the zone of incidence 4 on the specimen surface 3 to be etched. The plane 10 and/or the cone 11 with their central axis Z, Z' can be oriented perpendicularly to the specimen surface 3, or can be arranged tilted by an angle β with respect to the normal N of the specimen surface 3, as is schematically illustrated in FIGS. 5 and 6. As soon as the desired specimen thickness to be examined or etched-off surface with the zone of incidence 4' is reached, the etching operation can be terminated, and the specimen 1 can be viewed in a high resolution with the aid of the TEM in the viewing direction 12. The viewing direction 12 leads to the viewing surface 20 which is identical to the etched-off specimen surface 3 and thus to the zone of incidence 4' of the ion beams J at the end of the etching operation.

Figure 1:
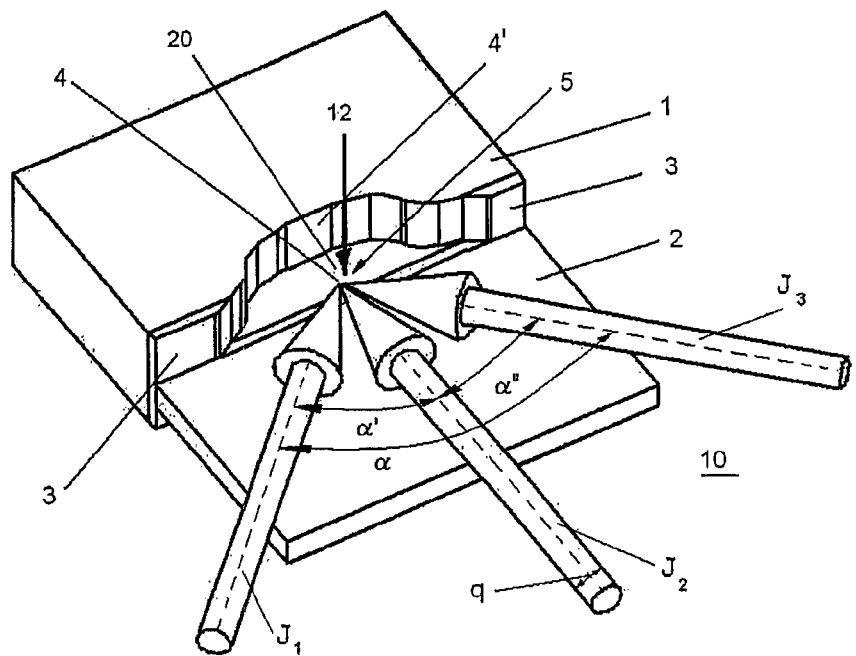
FIG. 1 shows a specimen in a three-dimensional illustration for the slope etching with three ion beams lying in one plane according to the invention.

An arrangement with a specimen 1 is schematically illustrated for the slope etching method in FIG. 1. The present method is particularly suitable for the more complex and more delicate slope etching method. The specimen 1 is cut out of the material to be examined. A plane mask 2 is brought close to a chosen specimen surface 3, the face of the mask being advantageously arranged perpendicularly to the specimen surface. The mask is somehow spaced from the specimen surface 3, which follows at a distance in the range between 10 μm and 100 μm, and as a result thereof, the two surfaces form a bordering line in this area. In the area of this line the zone of incidence 4 of the at least two, preferably three, ion beams $J_1$, $J_2$ with their beam diameter q is placed. The ion beams J lie in one plane 10, and the plane runs through this line. This plane 10 with the ion beams is advantageously positioned perpendicularly to the specimen surface 3 and can lie parallel to the surface of the mask 2. The plane 10 can also be arranged slightly tilted with respect to the surface of the mask 2 by an angle in the range between 0° and 10°, preferably between 0° and 5°. As a result thereof, depending on the specimen material to be processed and the desired result to be viewed the etching process can be optimally adjusted.

By way of the etching process, which follows now, and starting out at the zone of incidence 4 of the original specimen surface 3, the material is preferably removed in the direction of the ion beams J from the specimen 1, as a result whereof, some kind of a trench is formed with the zone of incidence 4' now lying at a lower position. The zone of incidence 4, 4' is thus displaced depending on the progress of the etching operation. To the side of the plane 10 and thus to the side of the ion beams within the specimen 1, a slight etching likewise takes place by grazing or straying ions, and a so-called slope 5 is formed at the desired location to be viewed, which slope forms the illustrated viewing surface 20. Given such a specimen, the viewing direction 12 for the SEM is advantageously oriented perpendicularly to the lateral specimen surface and in particular to the viewing surface 20.

In this preferred embodiment, the ion beams J are all oriented in one plane 10. These can enclose different angles α, α', α" and thus form some kind of a circle sector. In this connection, the spanned circle sector advantageously encloses an angle α which lies in the range between 10° and 180°, preferably in the range between 30° and 140°, and all ion beams lie in the plane 10 of this circle sector spanned by them. Depending on the number of ion beams, also further ion beams lie within the circle sector which is bounded by the two ion beams enclosing the largest angle and delimiting the circle sector. The ion beams can be oriented symmetrically or asymmetrically with respect to a normal N to the specimen surface, as schematically illustrated in FIGS. 5a to 5c. The so formed circle sector with the central axis Z can also additionally be tilted with respect to this normal N by an angle β for further settings of desired etching conditions. Here, the angle β advantageously lies in the range of ±20°, preferably in the range of ±10°.

Figure 4:
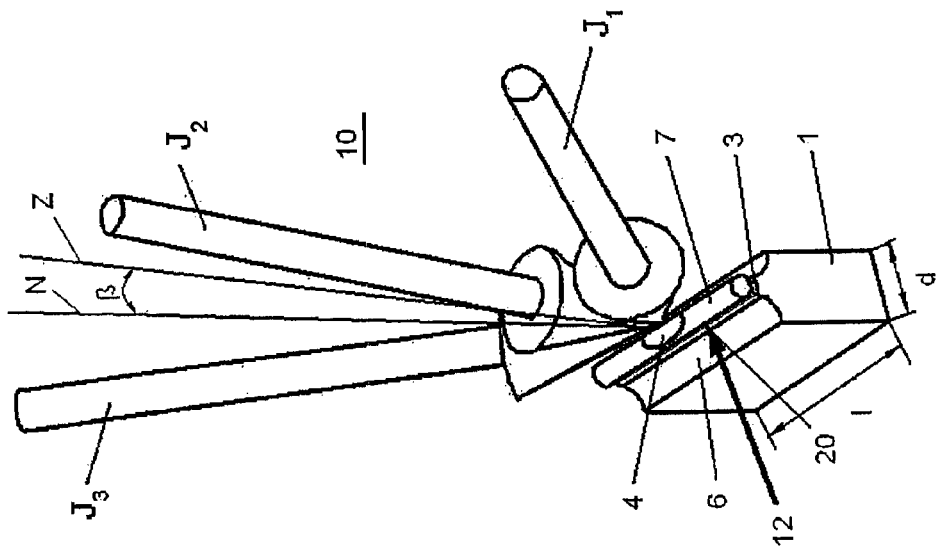
FIG. 4 shows a specimen in a three-dimensional illustration according to FIG. 3 in a rotated view and with no ion beam impinging perpendicularly.
Figure 3:
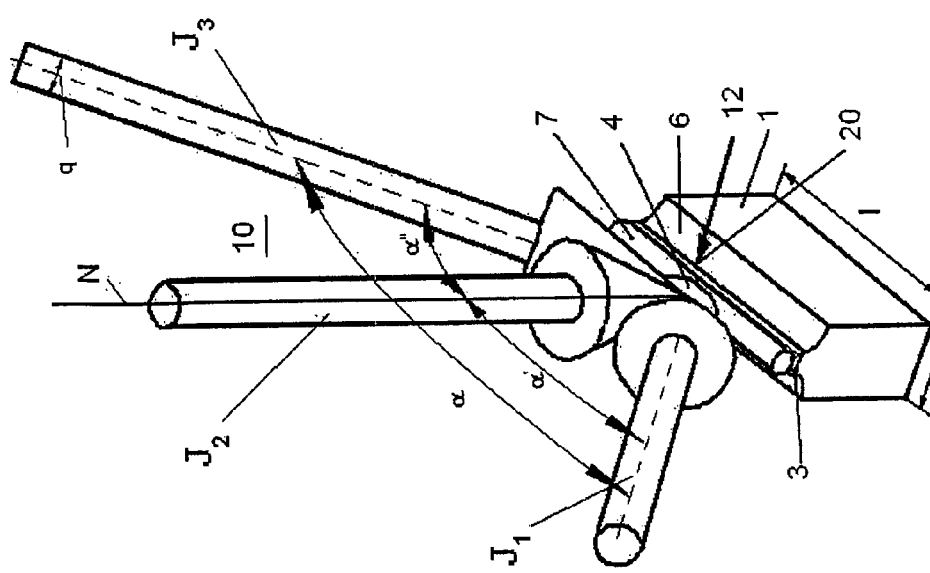
FIG. 3 shows a specimen in a three-dimensional illustration for the wire shadow method with three ion beams lying in one plane according to the invention, one ion beam impinging perpendicularly to the specimen surface.

In FIGS. 3 and 4, an assembly according to the wire shadow method is illustrated, which likewise represents a preferred mode of preparation for the present method. The figures show two different views in which the specimen 1 is illustrated in a slightly rotated manner for better clarity.

A specimen body is cut out of the specimen material, for example, with a diamond saw, such that an elongated specimen body 1 is formed with the length 1 and the width d. If the specimen is one cut from a microelectronic wafer, this specimen 1 often has a structured surface 3 which can additionally comprise coatings or layer systems (not shown). A wire or a fiber 7 with a small predetermined diameter is fixed on the specimen surface 3, for example with an adhesive. It is common practice to choose a specimen width d of about 100 μm or less up to 10 μm. The fiber to be applied has a diameter smaller than the specimen width d and forms a mask. According to the present invention, now at least two, preferably three, ion beams J are directed, preferably perpendicularly to the specimen surface 3, onto the fiber 7, where then the zone of incidence 4 is located. In this case, the normal N lies within the plane 10. The plane 10 is arranged parallel to the direction of the wire or even goes through the wire axis.

After a certain etching time, flanks 6 are formed by the material erosion of the specimen 1 on both sides of the specimen 1, which flanks form the viewing surface 20 for the TEM at the end of the etching operation. It can also be seen that a crest-like tapering of the specimen is formed, as can be seen in FIGS. 3 and 4. The specimen 1 is etched off by the ion beams J to such an extent that a clear wedge-form formation is generated transversely to its length 1. The etched flanks 6 on both sides of the specimen 1 now include an elongated crest which tapers to a point and, in this region, is transmissive to electrons for a TEM viewing which takes place from the side of the specimen, preferably in a perpendicular viewing direction 12, which is depicted by an arrow transversely to the longitudinal direction of the specimen. In this state, the fiber 7 is also intensively etched away.

Here too, by the ion beams, as previously described in the case of slope etching, some kind of a circle sector is formed within the plane 10, and the ion beams can impinge on the specimen surface 3 directed thereat at different angles, or can be arranged tilted as a whole. In this connection, the spanned circle sector advantageously encloses an angle α lying in the range between 10° and 180°, preferably in the range between 30° and 140°, and all ion beams lie in the plane 10 of this circle sector spanned by the ion beams. Depending on the number of the ion beams, also further ion beams lie within the circle sector which is bounded by the two ion beams that enclose the afore-mentioned largest angle and delimit the circle sector.

The ion beams can be oriented symmetrically or asymmetrically with respect to a normal N to the specimen surface, as schematically illustrated in FIGS. 5a to 5c. The so formed circle sector with the central axis Z can additionally also be tilted with respect to this normal N by an angle β for further settings of desired etching conditions. Here, the angle β is advantageously chosen in the range of ±20°, preferably in the range of ±10°.

FIGS. 5a to 5b schematically illustrate different possible positions and directions of incidence of ion beams J which, lying in one common plane (10), are guided with respect to the specimen surface. In FIG. 5a, the circle sector delimited by two ion beams $J_1$, $J_2$ at the angle α with respect to one another lies with its central symmetrical axis Z on the normal N to the specimen surface 3 on which the zone of incidence 4 for all ion beams J lies and in which these are converged in some kind of intersection point. Given this symmetrical arrangement, the two ion beams $J_1$, $J_2$ are guided in the direction of the zone of incidence at the angle α/2 with respect to the central axis Z or the normal N. When a third ion beam $J_3$ is used, it lies within the circle sector at the angles α' and α" with respect to the two outermost ion beams $J_1$, $J_2$ enclosing the circle sector. Further ion beams can lie within the circle sector.

The circle sector with the central axis Z can be arranged tilted with respect to the normal N by an angle β, i.e. have a certain asymmetry, as illustrated in FIG. 5b. A tilting where all ion beams will lie on one side of the normal N is illustrated in FIG. 5c. These arrangements are suited for all three applications, however, in particular for the slope etching method and for the wire shadow method.

For the arrangement of at least three ion beams J for processing the standard TEM specimens that do not lie within one plane 10, the three ion beams J1-J3 are guided lying on a conical circumferential surface 11 at corresponding angles α, the top of which conical circumferential surface lies in the zone of incidence 4, as illustrated in FIGS. 6a to 6c. The possibilities of a tilting of the entire arrangement by the angle β of the central axis Z of the cone are analogous to the previous arrangement in one plane according to FIGS. 6a to 6c. With more than three ion beams, those with the smaller angle deviations lie within the cone.

Various ways of converging the at least two ion beams J in the area of the zone of incidence 4 are illustrated in top views in FIGS. 7a to 7d. The ion beams with their cross section q all lie within the same plane 10 and contact each other in the zone of incidence at least in accordance with the illustration in FIG. 7a. These all lie in one line within the plane 10 which intersects the zone of incidence 4. They can individually overlap one another according to FIG. 7b or can all overlap one another according to FIG. 7c or can contact and overlap one another according to FIG. 7d.

Figure 8:
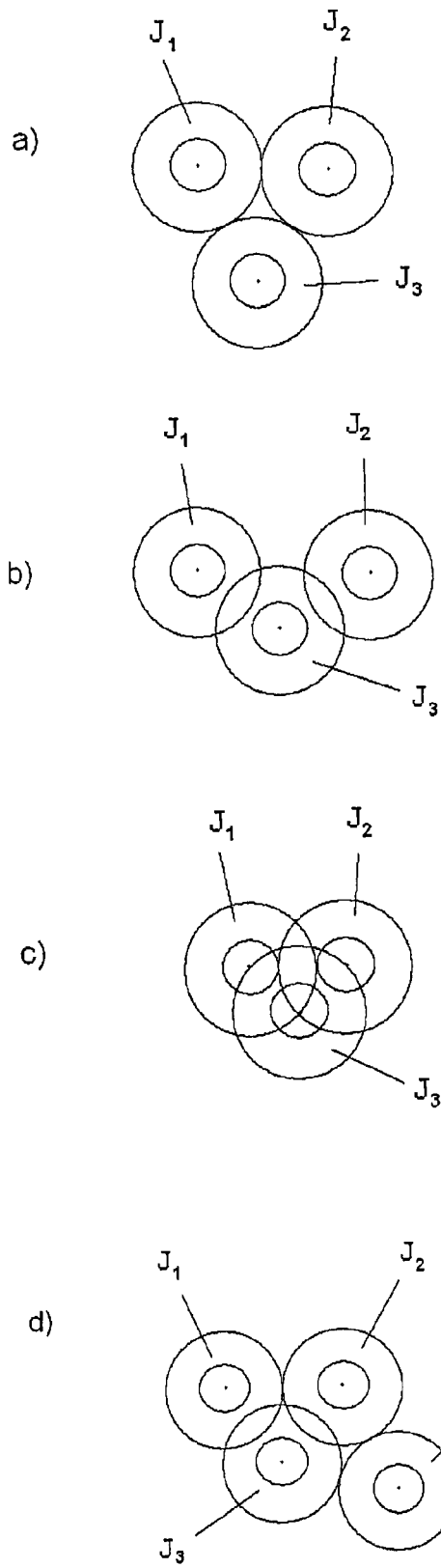
FIGS. 8a-d show, in top views of the specimen surface, different possible forms of the zone of incidence for several ion beams, given contacting and/or overlapping of ion beams not lying in one plane, for example lying on a conical circumferential surface.

The convergence of at least three ion beams J within a zone of incidence 4 for ion beams J which lie at least on a conical circumferential surface and/or even in between, is illustrated in FIGS. 8a to 8d. FIG. 8a shows three contacting ion beams $J_1$ to $J_3$ in the zone of incidence 4. Three partially overlapping ion beams are shown in FIG. 8b. Three overlapping ion beams are illustrated in FIG. 8c and four overlapping and contacting ion beams are shown in FIG. 8d.

The invention claimed is:

1. A method for producing a specimen for electron microscopy, comprising:
   guiding at least three stationary ion beams onto a specimen surface of the specimen at predetermined angles with respect to one another such that the at least three stationary ion beams at least contact or intersect one another on the specimen surface and form a zone of incidence at the specimen surface, wherein the specimen is cut out of a solid-state material with the specimen surface fowled thereon; and
   treating the specimen surface with the at least three stationary ion beams such that material of the specimen at an area of the zone of incidence is removed from the specimen surface by etching until a desired viewing surface is uncovered in the area of the zone of incidence,
   wherein the desired viewing surface is configured to allow viewing in a desired area of the specimen with an electron microscope, and
   wherein both the specimen and the at least three stationary ion beams are not moved such that the at least three stationary ion beams are operated stationarily during said treating of the specimen surface.

2. The method according to claim 1, wherein the treating of the specimen surface with the at least three stationary ion beams is in accordance with a slope etching method.

3. The method according to claim 1, wherein the treating of the specimen surface with the at least three stationary ion beams is in accordance with a wire shadow method.

4. The method according to claim 1, wherein the specimen is a standard TEM specimen having sides, wherein the treating of the specimen surface with the at least three stationary ion beams is performed such that the at least three stationary ion beams each are directed at least onto one of the sides of the TEM specimen for removal of the material of the specimen at the area of the zone of incidence.

5. The method according to claim 1, wherein the at least three stationary ion beams are guided onto the specimen surface at different incident angles, and wherein all of the at least three stationary ion beams at least contact one another in the zone of incidence.

6. The method according to claim 1, wherein positions of the at least three stationary ion beams in the zone of incidence are set such that a degree of overlapping is set for the etching.

7. The method according to claim 1, wherein at least two of the at least three stationary ion beams are generated jointly with one single ion source.

8. The method according to claim 1, wherein at least two of the at least three stationary ion beams are generated with their own respective ion source.

9. The method according to claim 1, wherein ion energy, ion current density, or a combination thereof for one of the at least three stationary ion beams is individually set, individually regulated, or a combination thereof for the treating of the specimen surface.

10. The method according to claim 1, wherein ion energy, ion current density, or a combination thereof of the at least three stationary ion beams are set to equal values or to predeterminable different values for the treating of the specimen surface.

11. The method according to claim 1, wherein a diameter of least one of the at least three stationary ion beams in the zone of incidence is set for the treating of the specimen surface.

12. The method according to claim 1, wherein, by varying at least one of ion energy, ion current, beam diameter, and a combination thereof of at least one of the at least three stationary ion beams, a predeterminable etching profile is set for the treating of the specimen surface.

13. The method according to claim 1, wherein ion energy of the at least three stationary ion beams is set in a range between 200 eV and 12 KeV for the treating of the specimen surface.

14. The method according to claim 1, wherein the specimen is at least temporarily viewed during the etching in high resolution with a viewing device.

15. The method according to claim 14, wherein the specimen is oriented prior to the etching with respect to the viewing device and is not moved any more during the etching.

16. The method according to claim 1, wherein the specimen is cooled during the etching.

17. The method according to claim 2, wherein, during the etching using the slope etching method, a mask having a plane surface is used, wherein the mask borders on the specimen surface at a distance in a range of 10 μm to 100 μm such that the plane surface and the specimen surface form a bordering line, wherein the zone of incidence of the at least three stationary ion beams lies in an area of the bordering line, wherein the at least three stationary ion beams span a plane in which the bordering line lies, wherein the plane is arranged slightly tilted with respect to the plane surface of the mask by an angle in a range between 0° and 10°, and wherein the plane surface of the mask is positioned perpendicularly to the specimen surface.

18. The method according to claim 2, wherein the at least three stationary ion beams span a circle sector having an angle which lies in a range between 10° and 180°, and wherein the at least three stationary ion beams lie in a plane of the circle sector.

19. The method according to claim 3, wherein the wire shadow method uses a wire, wherein, in the wire shadow method, the at least three stationary ion beams are guided in one plane which lies parallel to the wire, and wherein a normal to the specimen surface lies in the one plane.

20. The method according to claim 3, wherein the at least three stationary ion beams span a circle sector having a central axis, and wherein a plane of the circle sector is arranged to a normal of the specimen surface such that the central axis and the normal form an angle which lies in a range of ±20°.

21. The method according to claim 3, wherein the at least three stationary ion beams span a circle sector having an angle which lies in a range between 10° and 180°, wherein the at least three stationary ion beams lie in a plane of the circle sector, and wherein two of the at least three stationary ion beams are positioned symmetrically to surface normal during the treating of the specimen surface.

22. The method according to claim 4, wherein the at least three stationary ion beams are oriented lying on a conical circumferential surface on at least one side of the specimen, and wherein the at least three stationary ion beams are converged at a top of the cone and impinge on the zone of incidence on at least the at least one side of the specimen.

23. The method according to claim 1, wherein the at least three stationary ion beams are guided onto the specimen surface at different incident angles, and wherein all of the at least three stationary ion beams at least partially overlap one another in the zone of incidence.

24. The method according to claim 1, wherein a portion of the at least three stationary ion beams are guided onto the specimen surface at different incident angles, and wherein the portion of the at least three stationary ion beams at least contact one another in the zone of incidence.

25. The method according to claim 1, wherein a portion of the at least three stationary ion beams are guided onto the specimen surface at different incident angles, and wherein the portion of the at least three stationary ion beams at least partially overlap one another in the zone of incidence.

26. The method according to claim 1, wherein ion energy of the at least three stationary ion beams is set in a range between 500 eV and 8 KeV for the treating of the specimen surface.

27. The method according to claim 1, wherein the specimen is at least temporarily viewed during the etching in high resolution with one of a light microscope and a scanning electron microscope.

28. The method according to claim 1, wherein the at least three stationary ion beams consist of only three stationary ion beams, wherein the three stationary ion beams are guided onto the specimen surface at different incident angles, and wherein all of the three stationary ion beams at least contact one another in the zone of incidence.

29. The method according to claim 2, wherein, during the etching using the slope etching method, a mask having a plane surface is used, wherein the mask borders on the specimen surface at a distance in a range of 10 μm to 100 μm such that the plane surface and the specimen surface form a bordering line, wherein the zone of incidence of the at least three stationary ion beams lies in an area of the bordering line, wherein the at least three stationary ion beams span a plane in which the bordering line lies, wherein the plane is arranged slightly tilted with respect to the plane surface of the mask by an angle in a range between 0° and 5°, and wherein the plane surface of the mask is positioned perpendicularly to the specimen surface.

30. The method according to claim 2, wherein the at least three stationary ion beams span a circle sector having an angle which lies in a range between 30° and 140°, and wherein the at least three stationary ion beams lie in a plane of the circle sector.

31. The method according to claim 3, wherein the at least three stationary ion beams span a circle sector having a central axis, and wherein a plane of the circle sector is arranged to a normal of the specimen surface such that the central axis and the normal form an angle which lies in a range of ±10°.

32. The method according to claim 3, wherein the at least three stationary ion beams span a circle sector having an angle which lies in a range between 30° and 140°, wherein the at least three stationary ion beams lie in a plane of the circle sector, and wherein two of the at least three stationary ion beams are positioned symmetrically to surface normal during the treating of the specimen surface.

* * * * *